United States Patent
Higgins et al.

(10) Patent No.: US 10,799,414 B1
(45) Date of Patent: Oct. 13, 2020

(54) ORTHOTIC ANKLE GARMENT, AND METHOD FOR STABILIZING THE LOWER LEG OF A WEARER

(71) Applicant: Ortho 360, LLC, Elwood, IN (US)

(72) Inventors: David B. Higgins, Newton, NC (US); Pamela Pearl Haig, Kelley's Island, OH (US); Joe Haig, Kelley's Island, OH (US)

(73) Assignee: ING Source, Inc., Hickory, NC (US)

( * ) Notice: Subject to any disclaimer, the term of this patent is extended or adjusted under 35 U.S.C. 154(b) by 249 days.

(21) Appl. No.: 15/789,485

(22) Filed: Oct. 20, 2017

Related U.S. Application Data

(60) Provisional application No. 62/410,517, filed on Oct. 20, 2016.

(51) Int. Cl.
*A61H 1/00* (2006.01)
(52) U.S. Cl.
CPC ....... *A61H 1/006* (2013.01); *A61H 2201/165* (2013.01)
(58) Field of Classification Search
CPC ...... A61H 1/00; A61H 1/0237; A61H 1/0266; A61H 2201/164; A61H 2201/165; A61H 2203/0406; A61H 2205/12; A61H 2205/125; A61H 2205/106; A61H 1/006; A61H 39/04; A61H 9/092; A61F 5/01; A61F 5/0104; A61F 5/0102; A61F 5/0585; A61F 5/0111; A61F 5/0127; A61F 5/443; A61F 5/0195; A61F 13/0246; A61F 13/0253; A61F 13/066; A61F 13/067; A61F 2013/00238
USPC ........ 601/84, 5, 27, 104; 602/23, 27, 28, 30, 602/31, 36, 40, 44, 65, 66
See application file for complete search history.

(56) References Cited

U.S. PATENT DOCUMENTS

| | | | |
|---|---|---|---|
| 4,253,317 A | 3/1981 | Howard | |
| 4,729,370 A * | 3/1988 | Kallassy | A61F 13/066 602/65 |
| 5,617,745 A | 4/1997 | Della Corte | |
| 7,192,411 B2 | 3/2007 | Gobet et al. | |
| 7,434,423 B1 | 10/2008 | Reid, Jr. | |
| 7,934,267 B2 | 5/2011 | Nordstrom | |
| 8,221,340 B2 | 7/2012 | Farrow | |
| 8,317,736 B2 | 11/2012 | Virkus | |

(Continued)

FOREIGN PATENT DOCUMENTS

DE  102006032223 A1   7/2007
WO  WO-2017173441 A1 * 10/2017 ............ A61F 5/0111

*Primary Examiner* — Valerie L Woodward
*Assistant Examiner* — Paige Kathleen Bugg
(74) *Attorney, Agent, or Firm* — Schwartz Law Firm, P.C.

(57) ABSTRACT

An orthotic ankle garment has an open leg end and a toe end, and includes at least one circumferential compression zone located between the open leg and toe ends of the garment. The compression zone has elastic yarns integrated with the body yarn, and is adapted for applying substantially circumferential compression to the lower leg of the wearer. At least one low-stretch horizontal resistance band extends axially across the compression zone from a heel end of the resistance band to a toe end of the resistance band. The resistance band is adapted to reside substantially adjacent one side of the wearer's foot, and defines an area of reduced fabric stretch relative to directly adjacent areas of the ankle garment.

11 Claims, 8 Drawing Sheets

(56) References Cited

U.S. PATENT DOCUMENTS

| | | |
|---|---|---|
| 8,495,765 B2 | 7/2013 | Araki |
| 8,973,411 B2 | 3/2015 | Gaither |
| 9,204,986 B2 | 12/2015 | Higgins |
| 2002/0000002 A1* | 1/2002 | Hatch .................. A41B 11/00 2/239 |
| 2003/0083603 A1* | 5/2003 | Nelson .................. A61F 5/0111 602/27 |
| 2003/0230121 A1* | 12/2003 | Yokoyama ........... A41B 11/003 66/178 A |
| 2006/0085894 A1 | 4/2006 | Yakopson et al. |
| 2006/0247566 A1 | 11/2006 | Gobet |
| 2007/0038167 A1* | 2/2007 | Tabron .................... A61F 5/012 601/152 |
| 2008/0234615 A1* | 9/2008 | Cook .................. A61F 13/0283 602/13 |
| 2009/0165190 A1* | 7/2009 | Araki ....................... D04B 1/02 2/240 |
| 2010/0249686 A1* | 9/2010 | Rushton .................. A61F 5/019 602/30 |
| 2010/0331749 A1* | 12/2010 | Powaser ............... A61F 5/0111 602/23 |
| 2011/0088145 A1* | 4/2011 | Harada .................. A61F 5/019 2/240 |
| 2012/0102625 A1 | 5/2012 | Klein |
| 2012/0180195 A1 | 7/2012 | Shull |
| 2012/0232453 A1* | 9/2012 | Cropper ................ A61F 5/3715 602/30 |
| 2012/0238929 A1* | 9/2012 | Grunden ............... A61F 5/0111 602/27 |
| 2012/0283611 A1* | 11/2012 | Matsuo .................. A41D 13/06 602/27 |
| 2013/0090586 A1* | 4/2013 | Dennis ................. A61F 13/066 602/27 |
| 2013/0096478 A1* | 4/2013 | Cureton .............. A61F 13/0213 602/43 |
| 2013/0204172 A1* | 8/2013 | Viehweg ............... A61F 5/0102 602/26 |
| 2013/0263629 A1* | 10/2013 | Gaither ................ A41B 11/003 66/185 |
| 2014/0052040 A1* | 2/2014 | Coates .................. A61F 13/067 602/28 |
| 2014/0058311 A1* | 2/2014 | Higgins ................ A61F 13/067 602/63 |
| 2014/0276321 A1* | 9/2014 | Sellitto ................. A61F 5/0127 602/29 |
| 2015/0018741 A1* | 1/2015 | Lieberson ............. A43B 7/144 602/28 |
| 2015/0119775 A1* | 4/2015 | Gildersleeve ......... A61F 5/0127 602/7 |
| 2015/0119781 A1* | 4/2015 | Ponce ................... A61F 5/0111 602/28 |
| 2015/0335460 A1* | 11/2015 | Weaver, II ................ A61F 5/01 602/7 |
| 2016/0081840 A1* | 3/2016 | Higgins .................... A61F 5/00 602/63 |
| 2016/0143788 A1* | 5/2016 | Hirsch ............. A61F 13/00038 602/65 |
| 2016/0166419 A1* | 6/2016 | Jones ....................... D04B 1/26 602/66 |
| 2016/0206462 A1* | 7/2016 | Iida ....................... A61F 13/066 |
| 2016/0206463 A1* | 7/2016 | Watson ..................... A61F 5/14 |
| 2016/0242946 A1* | 8/2016 | Gambardella ........ A61F 13/065 |
| 2017/0020707 A1* | 1/2017 | Duport .................. A61F 5/0111 |
| 2017/0056233 A1* | 3/2017 | Kelly ..................... A61F 5/0118 |
| 2017/0079847 A1* | 3/2017 | Tsuchiya ............. A61F 13/065 |
| 2017/0128237 A1* | 5/2017 | Rouse ...................... A61F 2/70 |
| 2017/0196737 A1* | 7/2017 | Riley .................... A61F 5/0111 |
| 2017/0239098 A1* | 8/2017 | Schettler .............. A61F 13/085 |
| 2017/0367865 A1* | 12/2017 | Truhill ................. A61F 5/0127 |
| 2017/0367868 A1* | 12/2017 | Ducharme ............. A63B 71/12 |
| 2017/0367898 A1* | 12/2017 | Ostan ................... A61F 13/023 |
| 2018/0021199 A1* | 1/2018 | Halbrecht .............. A61H 1/008 601/27 |
| 2018/0051401 A1* | 2/2018 | Giorgini ............. A41D 13/0543 |
| 2019/0105187 A1* | 4/2019 | Brown ................ A61F 5/05858 |
| 2020/0093628 A1* | 3/2020 | Sigurdsson ........... A61F 5/0111 |

* cited by examiner

ORTHOTIC ANKLE GARMENT, AND METHOD FOR STABILIZING THE LOWER LEG OF A WEARER

TECHNICAL FIELD AND BACKGROUND OF THE DISCLOSURE

The present disclosure relates broadly and generally to compression supports for the lower leg and foot, such as those used for general medical and athletic purposes. In one exemplary embodiment, the invention comprises a compression foot garment, and method for supporting the foot, arch and plantar sole of a wearer while preventing or minimizing elongation and collapse of the foot; allowing intrinsic muscles to relax and heal using decompression theories, applications and techniques.

The invention comprises an easy-on fit, continuous and stable support, and is fabricated of soft moisture-wicking fabric. The invention can be comfortably worn inside shoes (and under or over socks) or similar product while walking, resting or exercising for added protection, injury prevention, relief of symptoms or conditions associated with numerous pathologies and healing. In exemplary embodiments, the invention (i) supports the foot, (ii) decompresses the plantar sole, arch, intrinsic muscles and soft tissues, (iii) while boosting circulation as a pump to induce healing and repair of strained or injured soft tissues.

The invention incorporates knitted low-stretch resistance bands which cooperate to create a "taping effect" which contracts or decompresses the foot arch, thereby taking stress away from the plantar fascia. The resistance bands extend from an open toe end of the garment along opposite sides of the foot and around the back of the heel.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises an orthotic ankle garment or "sleeve" integrally knit of a body yarn (e.g., in circumferential courses and axial wales) and adapted for wear on a lower leg of a wearer. The orthotic ankle garment has an open leg end and an open (or closed) toe end, and further comprises at least one circumferential compression zone located between the open leg and toe ends of the garment. The compression zone has elastic yarns integrated with the body yarn, and is adapted for applying substantially circumferential compression to the lower leg of the wearer. At least one low-stretch horizontal resistance band extends axially across the compression zone from a heel end of the resistance band to a toe end of the resistance band. The resistance band is adapted to reside substantially adjacent one side of the wearer's foot, and defines an area of reduced fabric stretch relative to directly adjacent areas of the ankle garment.

The "lower leg" of the wearer comprises at least an ankle, heel and foot of the wearer. The foot comprises at least the calcaneus, lateral and medial malleolus, talus, midfoot, mid-tarsal joint, metatarso-phalangeal joints, and other bone structure. The portions of the lower leg, foot and foot anatomy are listed herein to provide antecedent basis for certain functional language recited in the claims and specification below. This listing is not intended to limit application of the exemplary ankle garment only to these portions of the lower leg, as parts of the ankle garment in other embodiments may extend around or over other portions of the ankle, heel, foot and leg.

The term "ankle garment" refers broadly herein to any hosiery or other fabric construction designed to cover at least a portion of the wear's foot. The ankle garment may be knit in whole or in part (e.g., using conventional circular knitting machinery), and may be specially designed for a variety of uses including running, cycling, hiking, golf, hunting, and other general athletic and every-day wear. The present ankle garment may comprise (or be integrally formed with) an open-toe sleeve, foot or ankle wrap, foot sock, tube sock, calf-high sock, mid-calf or over-the calf sock, crew sock, stocking, stretch or support hosiery, or the like.

The term "directly adjacent" in the context of the present disclosure means a fabric area (or "zone") located or formed beside or surrounded, in whole or in part, by another fabric area (or "zone") without intervening fabric, parts or other structure.

The term "axial" or "axial direction" refers herein to mean extending along a generally linear notional axis passing through circumferential portions (e.g., courses) of the garment. For example, the respective compression zones of the exemplary ankle garment may be axially divided—or divided along a generally vertical length such as from the heel upwardly towards the ankle or lower leg, and/or a generally horizontal length such as from the heel towards the toe.

The term "substantially equal" in the context of the present disclosure means within +/−10 percent.

The term "reduced fabric stretch" means having less stretch in at least one or both of a wale-wise and course-wise direction.

According to another exemplary embodiment, a skin-adhesive gel is applied to the toe end of the horizontal resistance band.

According to another exemplary embodiment, the low-stretch horizontal resistance band comprises a low-stretch medial resistance band extending axially across the compression zone, and adapted to reside substantially adjacent a medial side of the wearer's foot.

According to another exemplary embodiment, the low-stretch horizontal resistance band comprises a low-stretch lateral resistance band extending axially across the compression zone, and adapted to reside substantially adjacent a lateral side of the wearer's foot.

According to another exemplary embodiment, the compression zone comprises a first high compression zone axially spaced apart from the toe end of the ankle garment. The first high compression zone is adapted for applying at least 20 mmHg of substantially circumferential compression around a midfoot region of the wearer's foot. The exemplary ankle garment applies reduced compression axially from the first high compression zone towards the toe end of the garment.

According to another exemplary embodiment, the compression zone further comprises a second high compression zone axially spaced apart from the leg end of the ankle garment and adapted for applying at least 20 mmHg of substantially circumferential compression around the ankle of the wearer. The exemplary ankle garment applies reduced compression axially from the second high compression zone to the leg end of the garment.

According to another exemplary embodiment, the compression zone further comprises a first moderate compression zone formed at an anatomical turn of the ankle garment, and shaped to closely fit the heel and an upper instep region of the foot. The first moderate compression zone comprises a pressure release area between the first and second high compression zones, and configured to apply less circumferential compression to the foot as compared to the compression applied by the first and second high compression zones.

According to another exemplary embodiment, the compression zone further comprises a second moderate compression zone adjacent the first high compression zone and extending axially towards the toe end of the ankle garment. The second moderate compression zone is adapted for applying less circumferential compression to the foot as compared to the compression applied by the first high compression zone.

According to another exemplary embodiment, the compression zone further comprises a first light compression zone residing adjacent the second moderate compression zone at the toe end of the ankle garment. The first light compression zone is adapted for applying less circumferential compression to the foot as compared to the compression applied by the second moderate compression zone.

According to another exemplary embodiment, the compression zone further comprises a second light compression zone residing adjacent the second high compression zone at the open leg end of the ankle garment. The second light compression zone is adapted for applying less circumferential compression to the lower leg as compared to the compression applied by the second high compression zone.

According to another exemplary embodiment, the first light compression zone at the toe end of the garment comprises a flat-knit toe welt (or toe closure).

According to another exemplary embodiment, the second light compression zone at the open leg end of the garment comprises a folded ankle welt.

According to another exemplary embodiment, a width of the horizontal resistance band in a relaxed condition is greater than 0.75 inches and less than 1.5 inches.

In another exemplary embodiment, the present disclosure comprises an orthotic ankle garment integrally knit of a body yarn and adapted for wear on a lower leg of a wearer. The orthotic ankle garment has an open leg end and a toe end, and further comprises at least one circumferential compression zone located between the open leg and toe ends of the garment. The compression zone has elastic yarns integrated with the body yarn, and is adapted for applying substantially circumferential compression to the lower leg of the wearer. A low-stretch medial resistance band extends axially across the compression zone from a heel end of the medial resistance band to a toe end of the medial resistance band. The medial resistance band is adapted to reside substantially adjacent a medial side of the wearer's foot, and defines an area of reduced fabric stretch relative to directly adjacent areas of the ankle garment. A low-stretch lateral resistance band extends axially across the compression zone from a heel end of the lateral resistance band to a toe end of the lateral resistance band. The lateral resistance band is adapted to reside substantially adjacent a lateral side of the wearer's foot, and defines an area of reduced fabric stretch relative to directly adjacent areas of the ankle garment.

According to another exemplary embodiment, a skin-adhesive gel is applied to the toe end of the medial resistance band.

According to another exemplary embodiment, a skin-adhesive gel is applied to the toe end of the lateral resistance band.

According to another exemplary embodiment, a low-stretch arcuate heel lock is adapted for extending around a back of the heel, and is integrally knit with respective heel ends of the medial and lateral resistance bands. The exemplary heel lock defines an area of reduced fabric stretch relative to directly adjacent areas of the ankle garment. The width of the exemplary heel lock in a relaxed condition is between 0.75 and 1.5 inches.

In yet another exemplary embodiment, the present disclosure comprises an orthotic ankle garment integrally knit of a body yarn and adapted for wear on a lower leg of a wearer. The orthotic ankle garment has an open leg end and a toe end, and further comprises at least one circumferential compression zone located between the open leg and toe ends of the garment. The compression zone has elastic yarns integrated with the body yarn, and is adapted for applying substantially circumferential compression to the lower leg of the wearer. A low-stretch arcuate heel lock is integrated with the body yarn, and is adapted for extending around a back of the heel. The heel lock defines an area of reduced fabric stretch relative to directly adjacent areas of the ankle garment. At least one low-stretch horizontal resistance band extends axially across the compression zone from a heel end of the resistance band to a toe end of the resistance band, and is adapted to reside substantially adjacent one side of the wearer's foot. The resistance band defines an area of reduced fabric stretch relative to directly adjacent areas of the ankle garment.

According to another exemplary embodiment, the arcuate heel lock is integrally knit with the heel end of the horizontal resistance band.

In alternative exemplary embodiments, the medial and lateral resistance bands and/or arcuate heel lock may be separately or integrally formed (e.g., by knitting or weaving) with the body yarn of the ankle garment. Graduated compression within the various compression zones may be achieved by laying-in elastic yarns of strategic lengths or denier (thickness).

BRIEF DESCRIPTION OF THE DRAWINGS

Exemplary embodiments of the present invention will hereinafter be described in conjunction with the following drawing figures, wherein like numerals denote like elements, and wherein.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
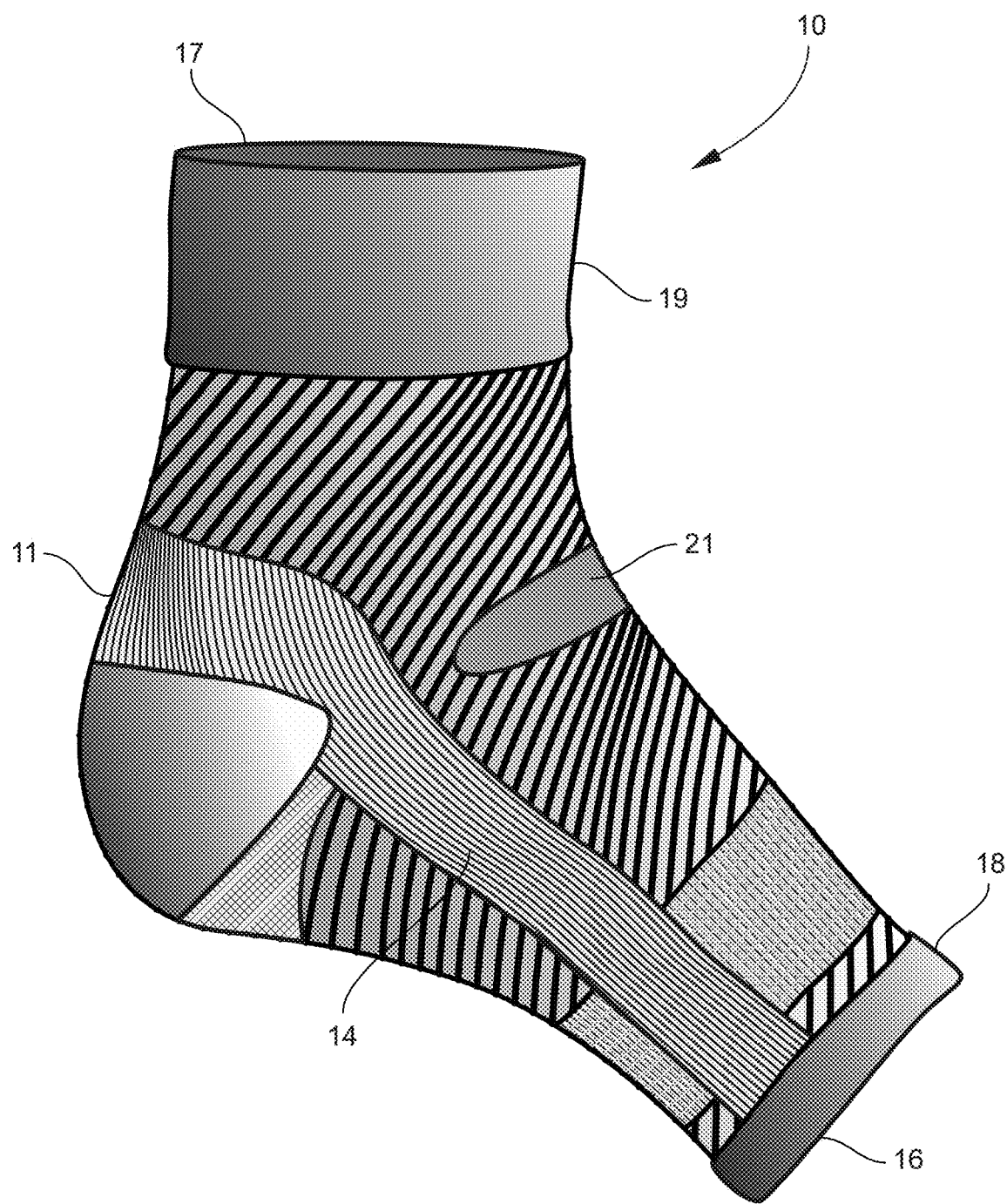
FIG. 1 is a view of the exemplary orthotic ankle garment showing various features and elements located on a lateral side (outer side) of the garment.
Figure 2:
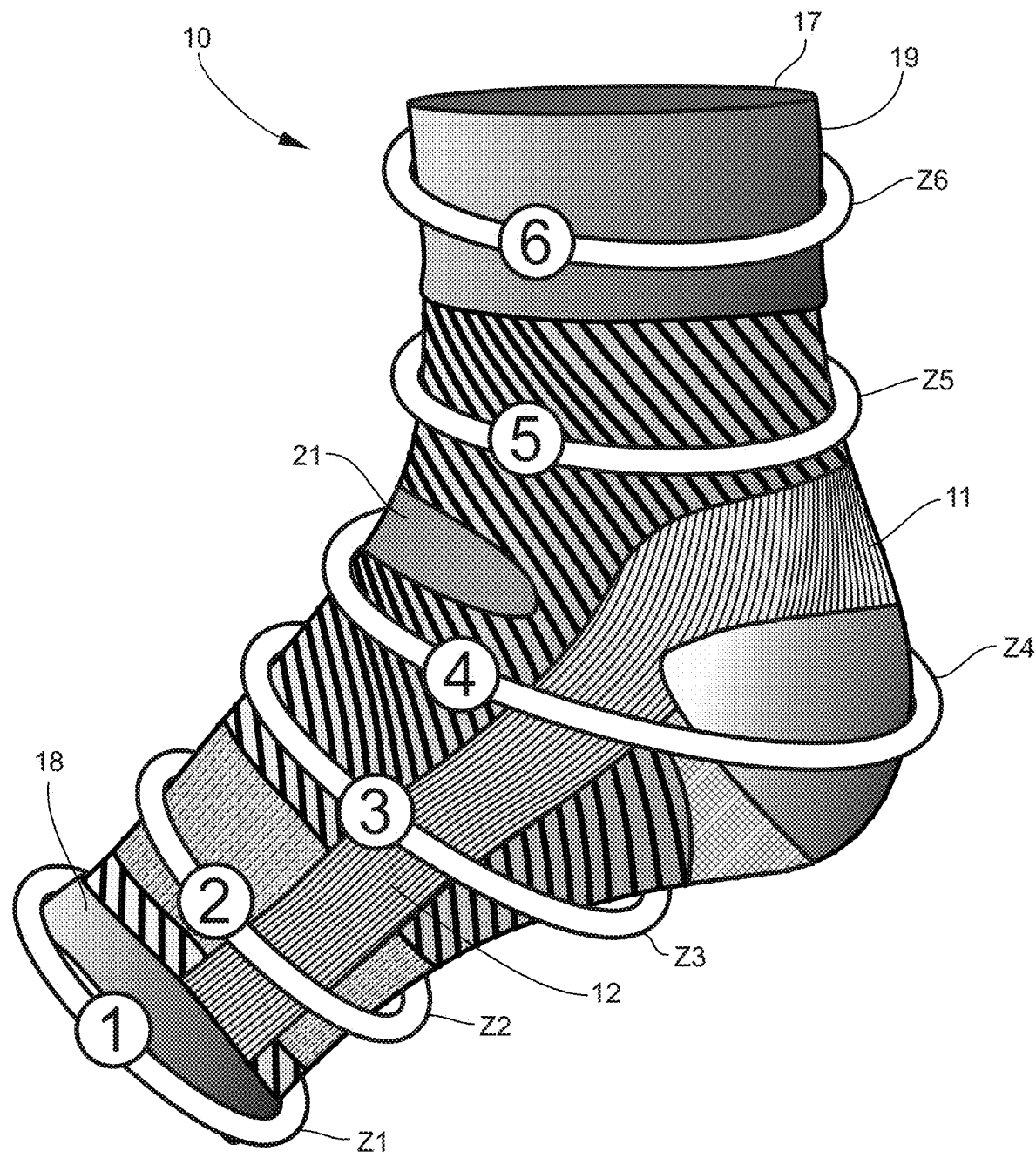
FIG. 2 is a view of the exemplary orthotic ankle garment indicating generally the various zones of circumferential compression.
Figure 3:
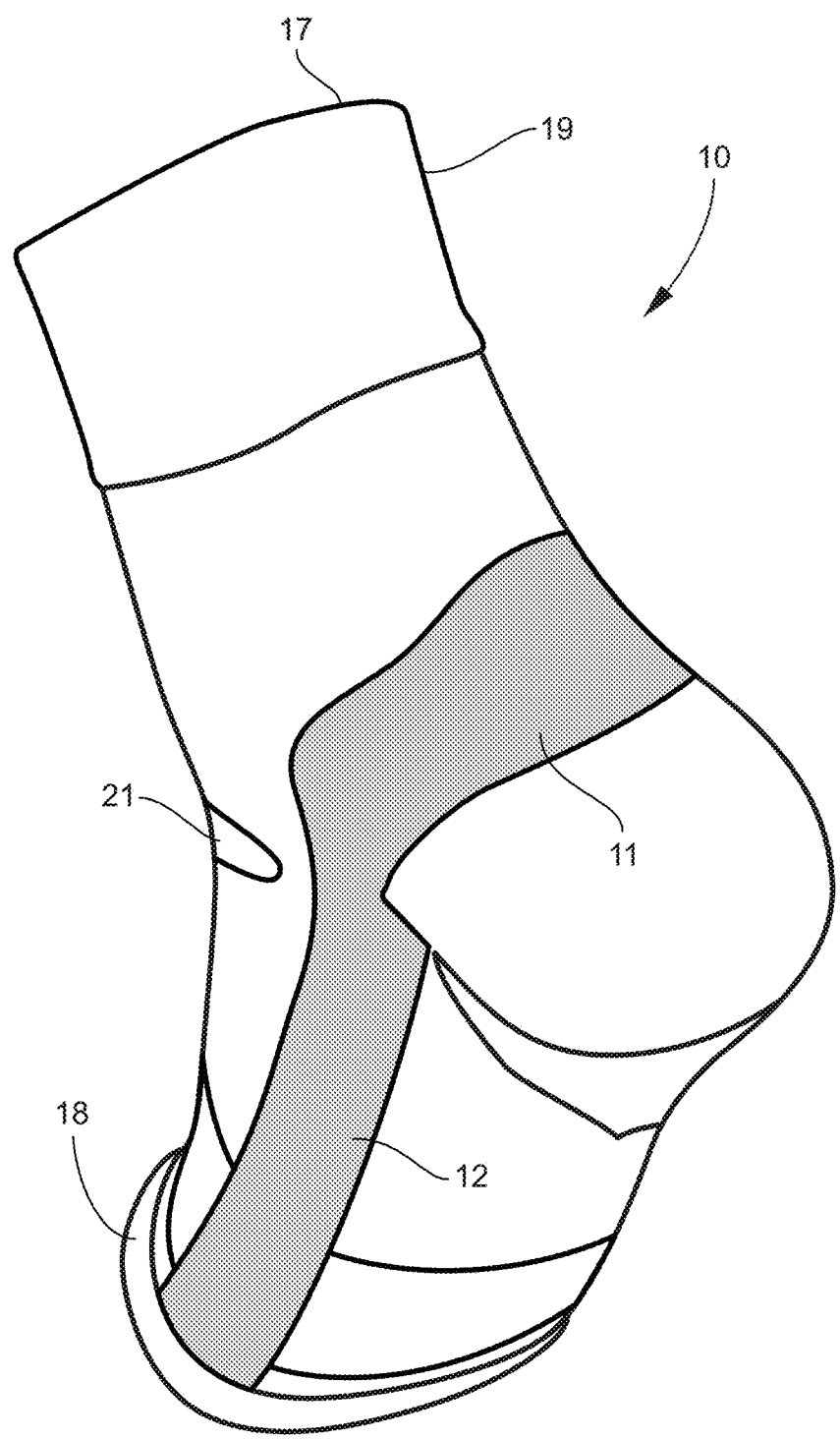
FIGS. 3 and 4 are rear medial and lateral perspective views of the exemplary ankle garment showing the heel lock and resistance bands in grayscale.
Figure 4:
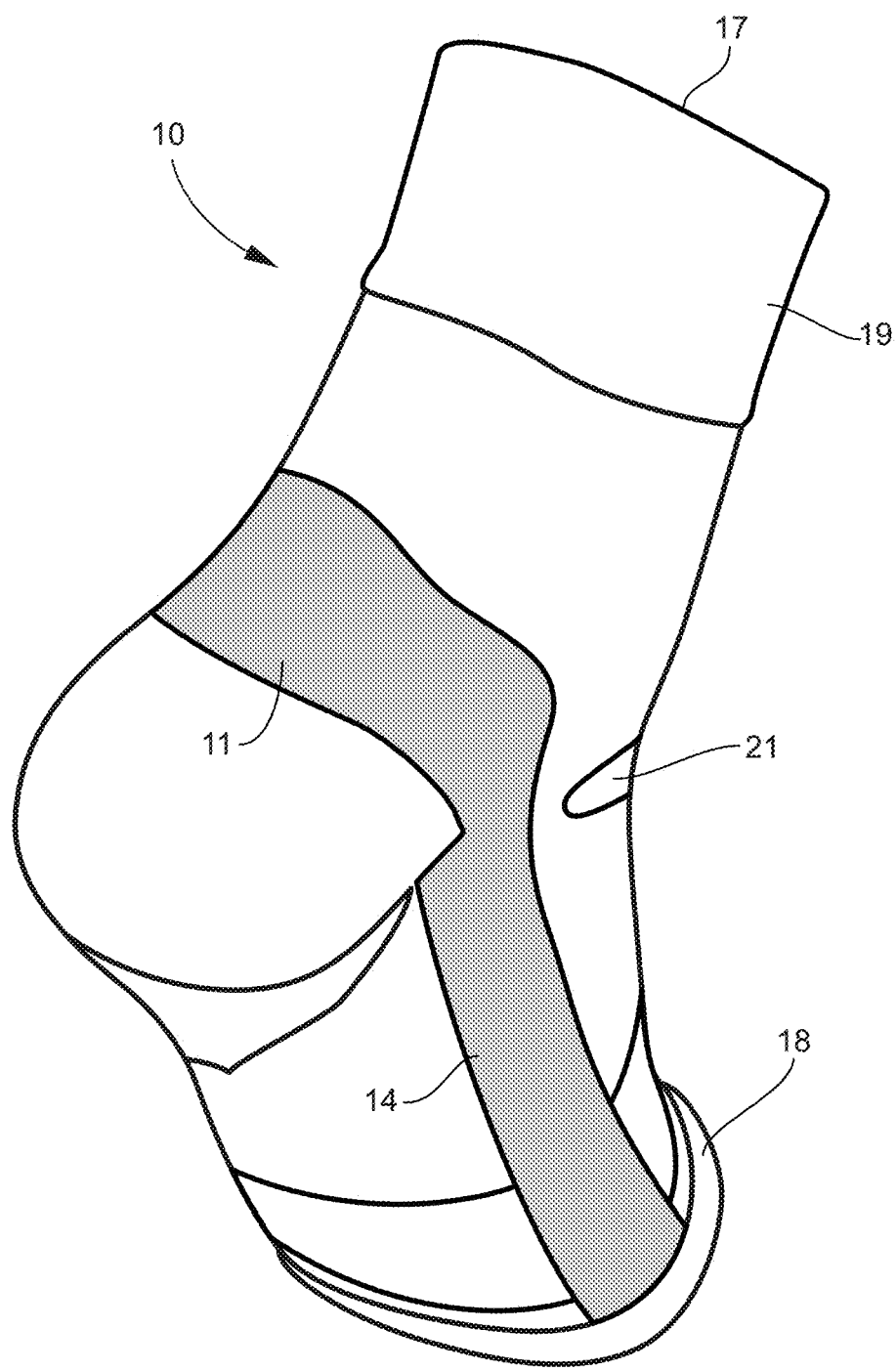
Figure 5:
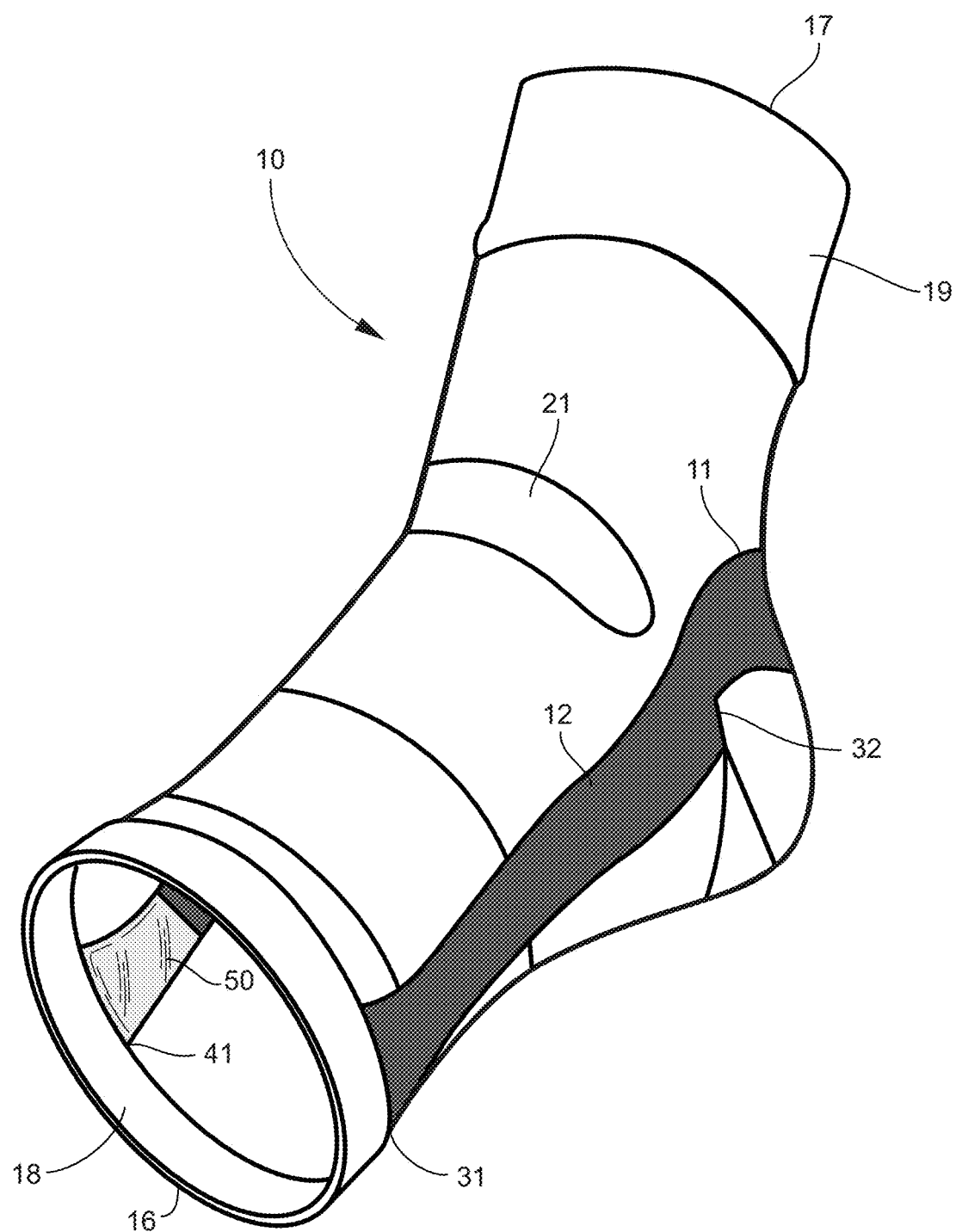
FIGS. 5 and 6 are front medial and lateral perspective views of the exemplary ankle garment showing the heel lock and resistance bands in grayscale.
Figure 6:
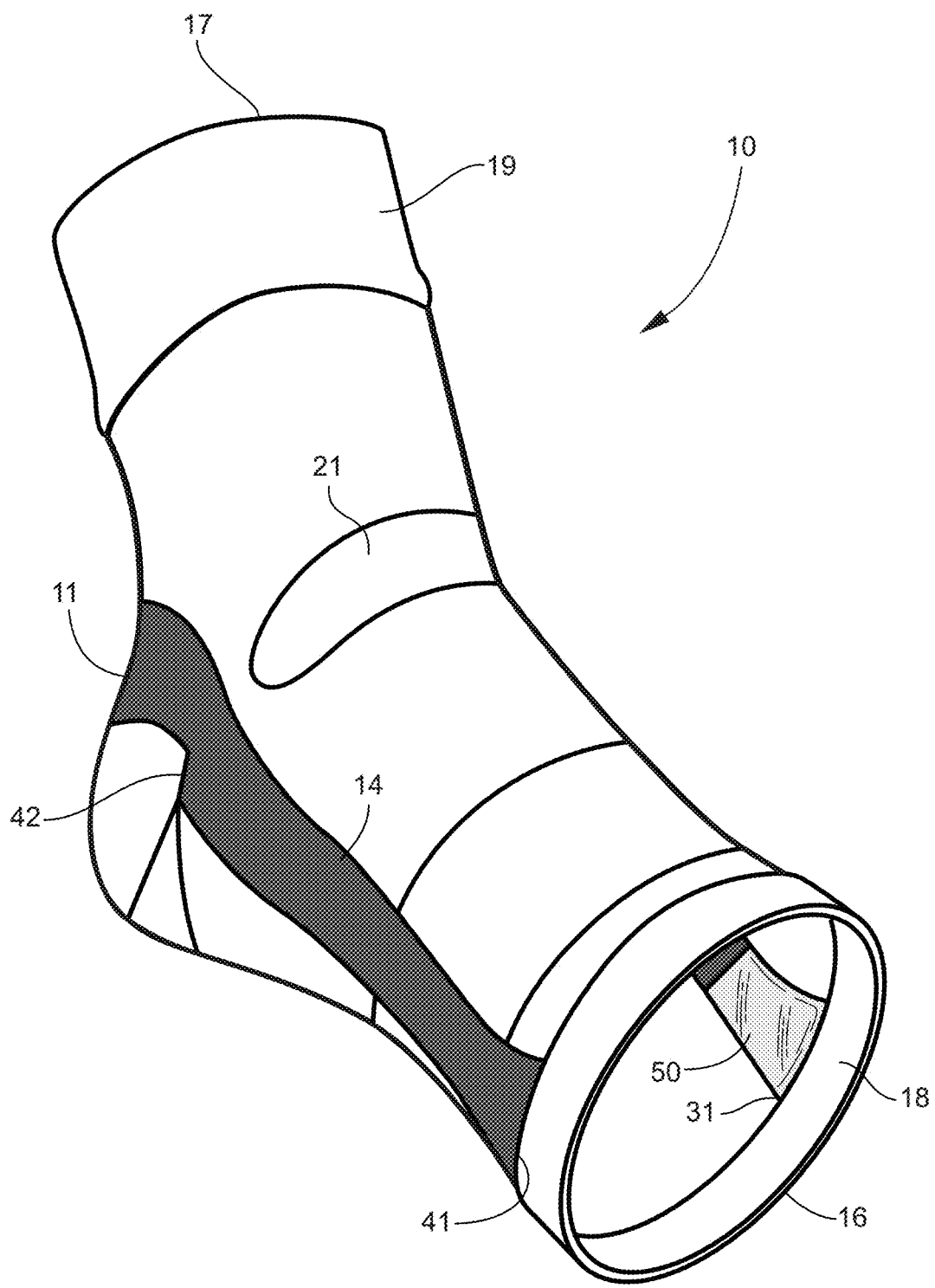
Figure 7:
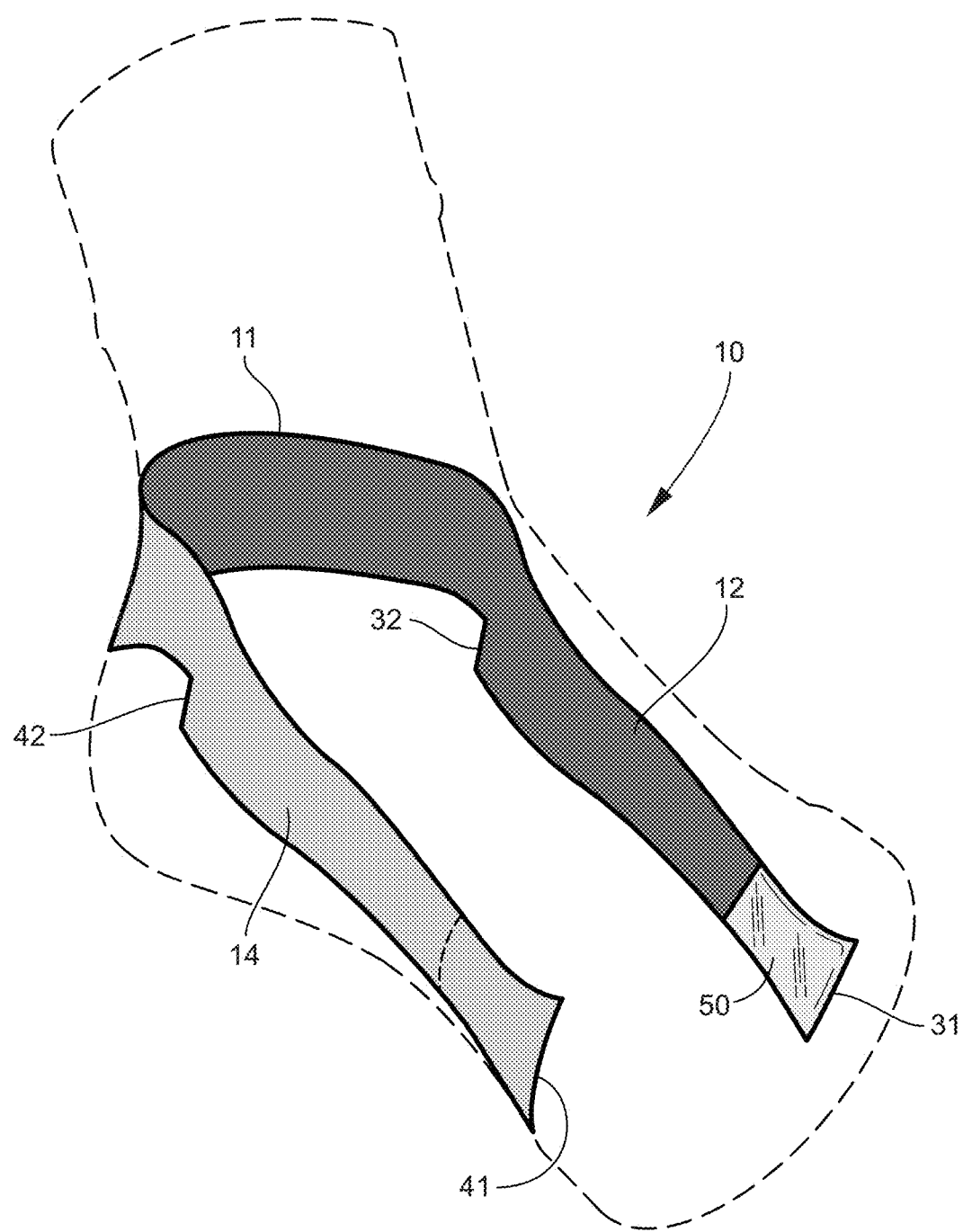
FIGS. 7 and 8 are further perspective views showing the heel lock and resistance bands of the exemplary ankle garment illustrated in phantom.
Figure 8:
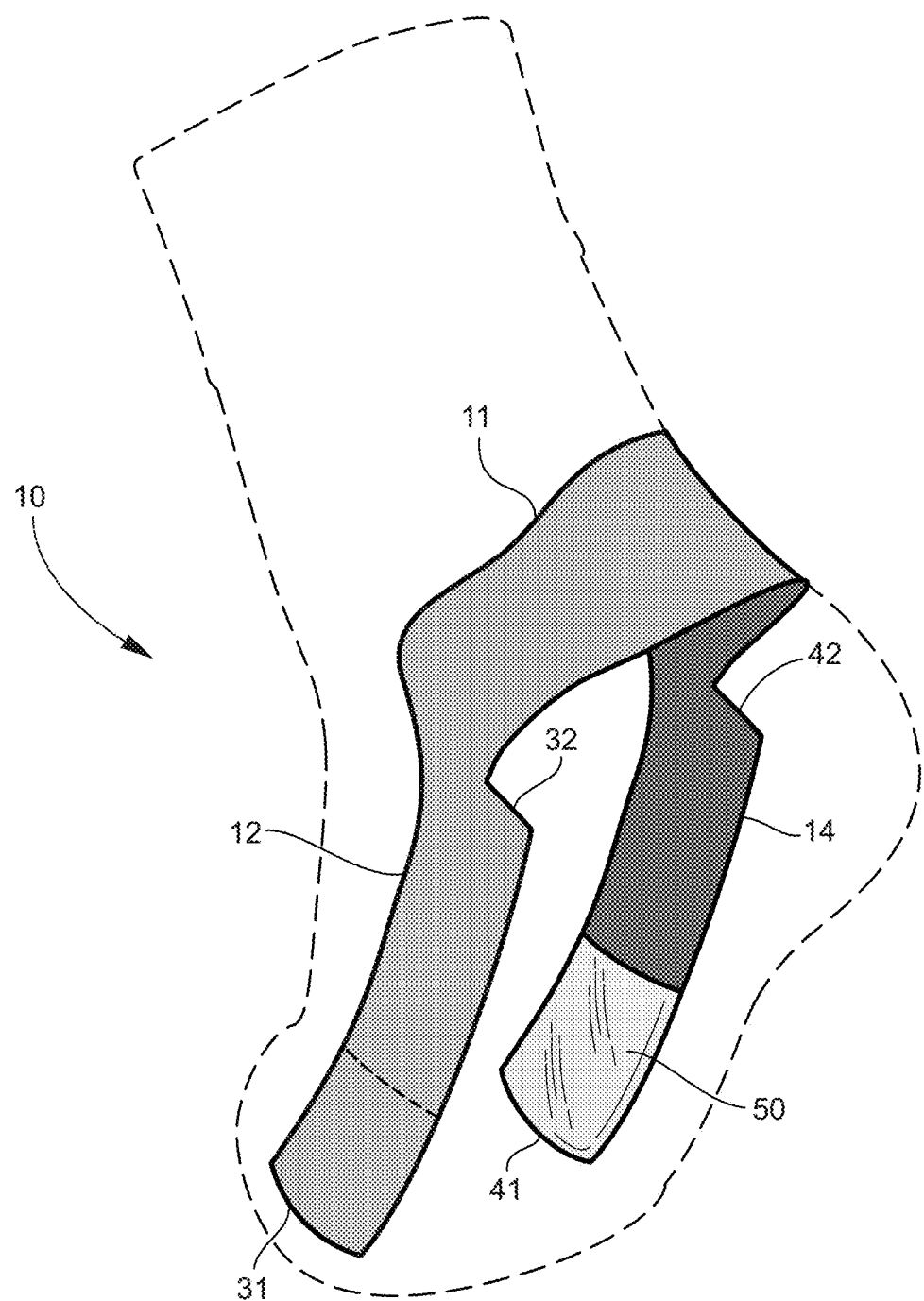

Referring now specifically to the drawings, a one-piece orthotic ankle garment according to one exemplary embodiment of the present disclosure is illustrated in FIGS. 1 and 2, and shown generally at broad reference numeral 10. The exemplary ankle garment 10 may be formed throughout of a closed-loop Jersey-knit body yarn comprising micro-nylon, moisture wicking fibers, and/or other natural or synthetic fibers or fiber blends. Elastic yarns, such as a spandex or other elastomer, are laid-in the body yarn in predetermined areas of the ankle garment 10 to create multiple distinct zones of graduated circumferential compression. One exemplary construction comprises approximately 76% 140-denier micro-nylon and 24% 280-denier LYCRA® (spandex). In the exemplary embodiment, the present ankle garment 10 may be constructed on a circular hosiery knitting machine integrating a plurality of yarns formed in needle and sinker loops extending in circumferential courses and axial wales. As discussed further below (and best shown in FIGS. 3 and 4), the exemplary garment 10 incorporates a low-stretch arcuate heel lock 11 designed to extend around a back of the heel, and opposing low-stretch medial and lateral resistance bands 12 and 14 designed to reside (respectively) on medial and lateral sides of the wearer's foot.

One commercial example of a circular knitting machine capable of producing the present ankle garment may be the "CC4-MED" machine manufactured by Merz Maschinenfabrik GmbH of Hechingen, Germany. The CC4-MED comprises a 4-feed, high-efficiency, single-cylinder circular knitting machine for the production of various compression garments in compression classes I to III. The Merz positive feeders enable the feeding-in of inlay yarns to produce the desired compression with controlled feed-in yarn tension in each mesh course. Alternatively, the exemplary ankle garment 10 may be fabricated according to other known techniques, such as by cut-and-sew of elasticized fabric from pre-designed patterns, with flat lock stitching.

As shown in FIG. 2, the exemplary ankle garment 10 is divided into axially adjacent circumferential regions—identified as compression zones Z1-Z6. In the exemplary embodiment, the circumferential regions may be constructed and axially divided as described in U.S. Pat. No. 9,204,986 entitled "Compression Foot Garment, and Therapeutic Method for Reducing Heel Pain." The complete disclosure of this prior patent is incorporated herein by reference.

The circumferential regions Z1-Z6 define respective therapeutic zones of designated compression designed to closely and comfortably fit the garment 10 to the wearer, while strategically supporting the ankle, heel and foot. The circumferential zones Z1-Z6 of the exemplary garment 10 are located to apply predetermined degrees of compression to various parts of the lower leg. Targeted compression in zones Z1-Z6 may be graduated by laying-in or "integrating" elastic yarns of strategic lengths or denier (thickness) with the body yarn of the garment 10 in the different axially-divided garment regions. In one exemplary embodiment, garment regions Z1 and Z6 comprise zones of relatively light compression, garment regions Z2 and Z4 comprise zones of relatively moderate compression (region Z4 comprising a "pressure release" area), and garment regions Z3 and Z5 comprise zones of relatively high or "firm" compression.

The knit construction in light compression zones Z1 and Z6 includes elastic yarns laid-in body yarns of the ankle garment 10, and increasing in length in a course-to-course axial direction towards to an open toe end 16 and leg end 17 of the garment 10. Exemplary zone Z1 defines a non-binding flex band or "welt" 18, and is knitted from 0.5-1.0 inch in relaxed axial width from the toe end 16 of the garment 10. Zone Z1 may comprise between 20-30 courses of body yarn, and may be configured to apply compression to the foot in the range of 10-15 mmHg, or less. Exemplary zone Z6 comprises a relatively wide, smooth and comfortable fabric band 15 with a relaxed axial width ranging from 1-3 inches from the open leg end 17 of the garment 10. In one specific exemplary embodiment, the relaxed width of the ankle garment in zone Z6 is 2.0 inches. This wide band 19 is designed to hold the garment 10 in place during wear, and may incorporate skin-adhering gels or other texture on its inside surface. The compression applied to the foot in zone Z6 may also be in the range of 10-15 mmHg, or less. The light compression zones Z1 and Z6 are designed to apply between 10%-50% less compression to the foot and ankle of the wearer as compared to the compression applied by the moderate compression zones Z2 and Z4 discussed below.

The moderate compression zone Z2 resides directly axially adjacent the light compression zone Z1, and comprises elastic yarns laid-in the body yarn of the ankle garment 10. The elastic yarns are strategically formed to provide increased graduated compression in a course-to-course axial direction from the light compression zone Z1 towards the high compression zone Z3. In the exemplary ankle garment 10, moderate compression zone Z2 may comprise between 40-60 courses of body yarn. The moderate compression zone Z2 is knitted from 1-2 inches in relaxed axial width, and may be designed to apply graduated circumferential compression to a forefoot of the wearer. According to one exemplary embodiment, the circumferential compression applied by moderate compression zone Z2 of the ankle garment 10 is in the range of 15-20 mmHg, and is between 10%-50% less compression as compared to that applied by high compression zones Z3 and Z5 in areas of the foot and ankle.

The high compression zone Z3 resides directly axially adjacent the moderate compression zone Z2, and comprises elastic yarns laid-in the body yarn in successive courses of the ankle garment 10. The high compression zone Z3 may be knitted from 1-2 inches in relaxed axial width, and may comprise between 40-60 courses of body yarn. In the exemplary embodiment, high compression zone Z3 applies graduated circumferential compression in the range of 20-30 mmHg to a midfoot of the wearer. This zone Z3 of the ankle garment 10 is designed to lift and support the plantar fascia (to promote "decompression" of the arch).

The high compression zone Z5 resides directly axially adjacent the light compression zone Z6, and comprises elastic yarns laid-in the body yarn in successive courses of the ankle garment 10. High compression zone Z5 may be knitted from 1-2 inches in relaxed axial width, and may comprise between 40-60 courses of body yarn. In the exemplary garment 10, compression zone Z5 is designed to apply graduated circumferential compression to the wearer's lower ankle in the range of 20-30 mmHg to engage and support the Achilles tendon.

The moderate compression zone Z4 comprises a "pressure release" area formed (e.g., jersey knit or other loop construction) between and directly axially adjacent high compression zones Z3 and Z5 at the anatomical turn of the garment 10, and is shaped to closely fit the heel and upper instep of the foot. The garment heel in this region has a deep-formed pocket made via reciprocation (knitting on one side). The upper instep has an oval shaped area 21 of thinner fabric which may be substantially devoid of elastic yarns to minimize bunching and thickness at the turn of the foot and ankle. Compression in this pressure release zone Z4 may be less than 15 mmHg.

Exemplary Low-Stretch Heel Lock 11 and Resistance Bands 12 and 14

Referring to FIGS. 2-8, the low-stretch heel lock 11 and medial and lateral resistance bands 12, 14 are integrally formed (e.g., by knitting or weaving) with the body yarn of the ankle garment 10, and are designed to extend collectively and continuously in a generally U-shaped configuration around a back of the heel, around the protruding medial and lateral malleoli of the ankle, and along respective medial and lateral sides of the foot. When properly worn, the heel lock 11 of ankle garment 10 extends around the heel and terminates generally at the lateral and medial malleoli of the ankle. The low-stretch medial resistance band 12 is integrally formed with the heel lock 11, and extends axially across the compression zones Z2-Z4 (FIG. 2) from a toe end 31 of the medial resistance band 12 to a heel end 32 of the medial resistance band 12. The heel end 32 resides substantially adjacent (but without entirely covering) the medial malleolus of the ankle, while the toe end 31 extends generally to the 1st metatarsal head of the wearer's foot. The low-stretch lateral resistance band 14 is likewise integrally formed with the heel lock 11, and extends axially across the compression zones Z2-Z4 from a toe end 41 of the lateral resistance band 14 to a heel end 42 of the lateral resistance band. The heel end 42 resides substantially adjacent (but without entirely covering) the lateral malleolus of the ankle, while the toe end 41 extends generally to the 5th metatarsal head of the wearer's foot.

In one exemplary embodiment, the low-stretch heel lock 11 and resistance bands 12, 14 are integrated into the ankle garment 10 using a "locked down" knitting technique feeding multiple ends through a single feed. The resulting increased body yarn and flattened (tightly closed) loops define fabric areas of up to 50% reduced stretch in both the course-wise and wale-wise directions, as compared to the immediately surrounding fabric structure of the garment 10. The low-stretch heel lock 11 and resistance bands 12, 14 function in a manner similar to low stretch athletic tape, such as that used for therapeutic taping to create motion control in injured limbs or to prevent injury in performing athletes or ambulatory patients. In the exemplary ankle garment 10, the width of the heel lock 11 and resistance bands 12, 14 in a relaxed condition is greater than 0.75 inches and less than 1.5 inches.

As best shown in FIGS. 5-8, a skin-adhesive gel 50 may be located on an inside of the fabric at respective toe ends 31, 41 of the medial and lateral resistance bands 12, 14. In an exemplary embodiment, the skin-adhesive gel 50 comprises a low durometer silicone gel or other comparable substance or element capable of adhering to the skin. The exemplary gel 50 may be applied to the garment 10 in a hot liquid form using a screen and pressing bar, such that a thin layer of the material melts, absorbs, and fuses into the fabric. The fabric is then heated to cure the gel 50, thereby permanently integrating and locking it into the garment 10. In one embodiment, the gel 50 is located on the resistance bands 12, 14 entirely and exclusively in compression zone Z2 of the ankle garment to reside adjacent a medial midfoot region (at base of the first metatarsal to distal, or bisecting the first metatarsal head) and a lateral midfoot region (at the base of the $5^{th}$ metatarsal to distal, or bisecting the $5^{th}$ metatarsal head). In alternate embodiments, the skin-adhering gel 50 may be applied to the resistance bands 12, 14 throughout compression zone Z2 and some or all of compression zone Z3 of the garment 10.

When the ankle garment 10 is worn on a bare foot, the gel 50 adheres to the skin in a similar fashion to athletic tape, and cooperates with the low-stretch heel lock 11 and resistance bands 12, 14 to create a pulling or stabilizing force on the wearer's foot. When properly worn, the exemplary ankle garment 10 comprises an orthopedic structure offering semirigid medial and lateral resistance to the medial and lateral forefoot, distal midfoot and heel. The exemplary garment 10 may promote a "decompression" of the arch and foot structure in girth and length, thereby reducing tension on the plantar tissues and intrinsic muscle structure of the foot between the metatarsal heads (dorsal, medial, lateral and plantar) and the calcaneus (heel), and the insertions of extrinsic muscles within the foot. In other exemplary embodiments not shown, the present ankle garment 10 may incorporate only one of the low-stretch heel lock and medial and lateral resistance bands, or any combination of two or more of the low-stretch heel lock and medial and lateral resistance bands.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

What is claimed:

1. An orthotic ankle garment integrally knit of a body yarn and adapted for wear on a lower leg of a wearer, the lower leg including an ankle, heel and foot comprising a foot arch, said orthotic ankle garment having an open leg end and a toe end, and further comprising:
   at least one circumferential compression zone comprising elastic yarns integrated with said body yarn, and located between the open leg and toe ends of said garment, and said compression zone adapted for applying substantially circumferential compression to the lower leg of the wearer;
   a low-stretch medial resistance band extending axially across said compression zone from a heel end of said medial resistance band to a toe end of said medial resistance band, and adapted to reside substantially adjacent a medial side of the wearer's foot proximate a 1st metatarsal head of the wearer's foot, and said medial resistance band defining an area of reduced fabric stretch relative to directly adjacent areas of said ankle garment;
   a low-stretch lateral resistance band extending axially across said compression zone from a heel end of said lateral resistance band to a toe end of said lateral resistance band, and adapted to reside substantially adjacent a lateral side of the wearer's foot proximate a 5th metatarsal head of the wearer's foot, and said lateral resistance band defining an area of reduced fabric stretch relative to directly adjacent areas of said ankle garment;
   a low-stretch arcuate heel lock adapted for extending around a back of the heel and integrally knit with respective heel ends of said medial and lateral resistance bands, and said heel lock defining an area of reduced fabric stretch relative to directly adjacent areas of said ankle garment, and wherein said low-stretch heel lock and said low-stretch medial and lateral resistance bands are designed to extend collectively and continuously in a generally U-shaped configuration around a back of the heel, around protruding medial and lateral malleoli of the ankle, and along respective medial and lateral sides of the foot; and
   a skin-adhesive gel applied to the toe ends of said medial and lateral resistance bands, such that when said orthotic ankle garment is worn by the wearer, said gel cooperates with said low-stretch arcuate heel lock and said medial and lateral resistance bands to create a pulling force on the foot thereby promoting decompression of the foot arch.

2. The orthotic ankle garment according to claim 1, wherein said at least one compression zone comprises a first high compression zone axially spaced apart from the toe end of said ankle garment and adapted for applying at least 20 mmHg of substantially circumferential compression around a midfoot region of the foot, and wherein said ankle garment comprises reduced compression axially from said first high compression zone towards the toe end of said garment.

3. The orthotic ankle garment according to claim 2, wherein said at least one compression zone further comprises a second high compression zone axially spaced apart from the leg end of said ankle garment and adapted for applying at least 20 mmHg of substantially circumferential compression around the ankle of the wearer, and wherein said ankle garment comprises reduced compression axially from said second high compression zone to the leg end of said garment.

4. The orthotic ankle garment according to claim 3, wherein said at least one compression zone further comprises a first moderate compression zone formed at an anatomical turn of said ankle garment, and shaped to closely fit the heel and an upper instep region of the foot, and said first moderate compression zone comprising a pressure release area between said first and second high compression zones, and configured to apply less circumferential compression to the foot as compared to the compression applied by said first and second high compression zones.

5. The orthotic ankle garment according to claim 4, wherein said at least one compression zone further comprises a second moderate compression zone adjacent said first high compression zone and extending axially towards the toe end of said garment, said second moderate compression zone adapted for applying less circumferential compression to the foot as compared to the compression applied by said first high compression zone.

6. The orthotic ankle garment according to claim 5, wherein said at least one compression zone further comprises a first light compression zone residing adjacent said second moderate compression zone at the toe end of said ankle garment, said first light compression zone adapted for applying less circumferential compression to the foot as compared to the compression applied by said second moderate compression zone.

7. The orthotic ankle garment according to claim 6, wherein said at least one compression zone further comprises a second light compression zone residing adjacent said second high compression zone at the open leg end of said ankle garment, said second light compression zone adapted for applying less circumferential compression to the lower leg as compared to the compression applied by said second high compression zone.

8. The orthotic ankle garment according to claim 7, wherein said second light compression zone at the open leg end of said garment comprises a folded ankle welt.

9. The orthotic ankle garment according to claim 1, wherein a width of said low-stretch medial resistance band in a relaxed condition is less than 1.5 inches.

10. The orthotic ankle garment according to claim 1, wherein a width of said low-stretch lateral resistance band in a relaxed condition is less than 1.5 inches.

11. The orthotic ankle garment according to claim 1, wherein a width of said low-stretch arcuate heel lock in a relaxed condition is less than 1.5 inches.

* * * * *